United States Patent [19]

Hahn et al.

[11] Patent Number: 4,873,079

[45] Date of Patent: Oct. 10, 1989

[54] HAIR COLORING COMPOSITION AND ITS METHOD OF USE

[75] Inventors: Charles R. Hahn, Cornwall-on-Hudson, N.Y.; Warren B. Shapiro, Norwalk, Conn.

[73] Assignee: Clairol Incorporated, New York, N.Y.

[21] Appl. No.: 132,500

[22] Filed: Dec. 14, 1987

Related U.S. Application Data

[63] Continuation of Ser. No. 88,163, Aug. 21, 1987, abandoned.

[51] Int. Cl.[4] .................................................. A61K 7/13
[52] U.S. Cl. .......................................... 424/70; 8/405; 8/426; 8/435
[58] Field of Search ................ 424/70; 8/405, 425, 8/426, 428, 429, 435

[56] References Cited

U.S. PATENT DOCUMENTS

| | | | |
|---|---|---|---|
| 2,983,651 | 5/1961 | Seemuller | 167/88 |
| 3,168,441 | 2/1965 | Bil et al. | 8/426 |
| 3,402,986 | 9/1968 | Zviak et al. | 8/10.1 |
| 3,449,056 | 6/1969 | Pum | 8/426 |
| 3,480,377 | 11/1969 | Lyons | 8/10.1 |
| 3,619,102 | 11/1968 | Zviak et al. | 8/10.1 |
| 3,632,290 | 1/1972 | Tucker et al. | 8/10.1 |
| 3,697,644 | 10/1972 | Laiderman | 424/70 |
| 4,391,603 | 7/1983 | Rosenbaum et al. | 8/405 X |

*Primary Examiner*—Ellis P. Robinson
*Assistant Examiner*—Susan S. Rucker
*Attorney, Agent, or Firm*—Charles J. Zeller

[57] ABSTRACT

A temporary or semipermanent hair coloring composition comprising an aqueous vehicle having incorporated therein a hair coloring component, said composition also containing as a cosolvent for the hair colorant from less than about 15% by weight of a diol selected from the group consisting of aliphatic hydrocarbon diols having from 5 to 8 carbon atoms and bis (hydroxyalkyl) cyclohexanes having from 7 to 14 carbon atoms.

13 Claims, No Drawings

HAIR COLORING COMPOSITION AND ITS METHOD OF USE

FIELD OF INVENTION

This is a continuing application of application Ser. No. 88,163, filed Aug. 21, 1987, now abandoned.

This invention relates to a temporary or semipermanent hair coloring composition and to a process for coloring hair that utilizes such compositions. More particularly, it concerns compositions and processes of the aforesaid character that employ certain diols as cosolvents in the hair coloring compositions.

BACKGROUND INFORMATION

In the preparation of temporary or semipermanent hair coloring compositions, it has become customary to include ethanol as a cosolvent for the colorants contained in these compositions. Generally, water is used as the principal component of the vehicle for such formulas. However, when ethanol is employed for this purpose, it has been found necessary to use as much as 33% by weight of ethanol based on the total weight of the colorant composition. This has proven to have several distinct disadvantages such as the excessive cost that it adds to the products.

INVENTION

It has now been found that certain diols defined in more detail below are more effective cosolvents for semipermanent or temporary hair colorants than ethanol. As a consequence, it has made it possible for the reduction of the quantity of cosolvent that needs to be employed. The advantages that flow from this are several. In the first place, this accomplishes a savings in the cost of the formulas. Furthermore, the absence of ethanol is of importance for the users of the product with black ethnic hair. Moreover, it has been found that better dye take on hair is often achieved when the diol cosolvents in this invention are employed in place of the ethanol.

PRIOR ART

U.S. Pat. No. 2,983,651 describes a composition for dyeing hair comprising a solution of a direct dye in an aqueous organic solvent. In this case, the organic solvent is an ether alcohol of the general formula R-(O-CH$_2$-CH$_2$)$_n$OH wherein R is an aliphatic hydrocarbon group.

U.S. Pat. No.3,402,986 describes a process for dyeing hair that uses a direct dye dispersed in an aqueous medium containing up to 10% by weight of a water miscible alcohol. Among the alcohols suggested for use are butyl alcohol, thioether alcohol (e.g. thiodiglycol), ketoalcohols (e.g. diacetone alcohol), aralkanols (e.g. benzyl alcohol, betaphenylethyl alcohol), carbocylic alcohols (e.g. cyclohexanol), and heterocyclic alcohols (e.g. furfuryl alcohol).

U.S. Pat. No.3,619,102 describes a composition for dyeing hair using an aqueous solution of a direct dye containing an ether alcohol of the formula

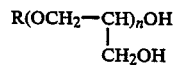

wherein R is a certain alkyl radical.

U.S. Pat. No.3,480,377 describes a process for dyeing hair with a dyeing composition comprising an aqueous solution, suspension or dispersion of a dye, an organic solvent and a dissolved aromatic compound. Among the organic solvents selected for use are cyclohexanol and hexylene glycol which are quite distinct from the diols employed in this invention.

U.S. Pat. No.3,632,290 discloses a process for dyeing hair with an aqueous composition containing a dye and ethyleneglycol phenyl ether.

Fr. Pat. No. 1,159,331 relates to a process for dyeing hair using an aqueous solution containing a dye and certain solvents. Among the solvents mentioned is cyclohexanol. In the alternative, this solvent may be used in conjunction with a certain ether alcohols.

It is clear from the summary of the above references that none of them would suggest the present invention to one skilled in this art.

DESCRIPTION OF INVENTION

The diols that are useful for the purposes of the present invention may be defined as diols selected from the group consisting of branched chain aliphatic hydrocarbon diols having from 5 to 8 carbon atoms and bis(hydroxyalkyl) cycloalkanes having from about 7 to 14 carbon atoms and, preferably, from about 8 to 12 carbon atoms. The cycloalkane moiety of said bis(hydroxyalkyl) cycloalkane will generally have from 5 to 6 carbon atoms in the ring with the preferred number being 6 carbon atoms. The alkyl moiety of said hydroxyalkyl groups on said cycloalkane ring will usually be a lower alkyl group containing from 1 to 4 carbon atoms.

A variety of diols falling within the above definition may be utilized in the practice of this invention. Illustrative of such diols that are employable herein are 2,2,4-trimethyl-1,3-pentanediol; 2,2-dimethyl-1,3-propanediol; 1,4-cyclohexanedimethanol, and 2-ethyl-1,3-hexanediol.

As indicated above, it is a feature of the present invention to substitute the diols defined above for the ethyl alcohol used in the hair dye preparation of the kind with which we are here concerned. Generally, about 33% of ethanol have been conventionally used in such products. When these diols are used, they are generally used at a concentration below about 15% by weight based on the weight of the total hair colorant composition. At the 15% level, separation of the product has been found to occur which may be a disadvantage. Generally, the concentration of the diol in the hair dye composition of this invention will be in the range of from about 2% to about 10% by weight based on the total weight of the hair colorant composition. However, the preferred range is about 3.5% to about 7.5% by weight of the diol on the same weight basis.

The hair colorants used in the composition of this invention can vary quite widely depending on the nature of the results desired. For the most part, the products will be temporary or semipermanent hair coloring products and the hair colorants selected for use will be of the direct dye variety, i.e. colorants that do not require oxidizing agents to develop their color. A large number of hair colorants are known in the prior art that can be used in the practice of this invention. Often, in order to obtain natural looking colors, it is desirable to blend two or more colorants. By way of illustrating particular colorants that are utilized herein the following are given below. Where CTFA nomenclature has been adapted for the colorant, these terms will be used to identify the colorant herein. Unless otherwise specified, where applicable, the definition of these colorants ar to be found in the CTFA Cosmetic Ingredient Dictionary, Third Edition, published by The Cosmetic, Toiletry and Fragrance Association, Inc. Suitable colorants include D&C Violet #2, D&C Orange #4, FD&C Yellow #6, Ext. D&C Violet #2, FD&C Red #4, FD&C Yellow #5, D&C Red #33, FD&C Blue #1, D&C Yellow #10, and D&C Green #5.

The quantity of colorant that may be contained in the hair coloring compositions of this invention may vary. Generally, the total quantity of colorant (where more than one colorant is employed this will be the total of all the colorants) that will be contained therein will be in the range of from about 0.001% to about 4% by weight based on the total weight of the colorant composition. In the preferred practice of this invention, this range will be from about 0.01% to about 2% on the same weight basis.

The principal vehicle of the composition of this invention will generally be an aqueous vehicle. The other components or adjuvants of these compositions will be dependent upon, at least in part, on the form that the product will take. A variety of product forms are available for the practice of this invention. These include solutions, creams, lotions, gels, foams, aerosols, etc.

The adjuvants of the compositions of this invention will be selected to accomplish a variety of purposes. These will include agents that function to improve the coloring operation or the ease of application. They may also be added to improve the physical or chemical stability of or the organoleptic qualities of the product. Typical of among such adjuvants are surfactants, viscosity adjusting agents, alkalizing agents, preservatives, film forming polymers, metal scavengers, organic acids, other cosolvents, fragrances, etc. By way of illustrating the specific adjuvants the following may be mentioned:

(1) Surfactants:
Nonoxynol-9
Nonoxynol-4
Sodium Lauryl Sulfate
Sodium Lauroyl Sarcosinate
Cocamidopropyl Betaine
Cocoamphocarboxypropionate
(2) Viscosity adjusting agents:
Cellosize
Methocel
Carbopol
Xanthan gum
Guar gum
(3) Alkalizing agents:
Diethanolamine
Ammonia
Ethanolamine
Tris (hydroxyethyl) Methyl Aminomethane
(4) Preservatives:
DMDM Hydantoin
Sorbic Acid
Methylparaben
Propylparaben
(5) Film Forming Polymers:
Polyquaternium Polymers
Polyvinylpyrrolidone
Gantrez
(6) Metal Scavengers:
EDTA
Disodium EDTA
(7) Organic Acids
Oleic Acid
Tall oil acid
Lactic acid
(8) Other cosolvents:
Carbitol
Propylene glycol
Hexylene glycol The procedures employed in preparing the products of this invention will vary depending on the particular product form. When, for example, the product takes the form of a solution, the following procedure can be employed: In a 1500 ml beaker, dissolve the thickener in about 60% of the total water for the batch with stirring until it becomes clear. Add the diol cosolvent, e.g., 2,2,4-Trimethyl-1,3-pentanediol which has been premixed with 20% of the total water. Continue to stir for about 10 minutes before adding any other ingredients. In a separate beaker (600 ml), dissolve the dyes, the acidifier and the surfactant. Mix well and combine the premixture while stirring. Continue stirring for about 20 minutes and then add fragrance. Continue to stir the batch for about 15 minutes, then bottle.

In the case where the product is formed into a gel, the following procedure may be employed: In a 1500 ml beaker with about 75% of the total water, dissolve the stabilizer, e.g., benzophenone-3, metalscavenger, preservative, e.g., phenoxyethanol and methylparaben, and dyes with stirring until all ingredients are in solution. Add the diol cosolvent that has been dissolved in 10% of the total water for the batch. Melt the surfactant, e.g., laureth-23, then mix with the fragrance and while stirring slowly add to batch. Increase the mixing speed slightly, slowly sprinkle in the thickener, e.g., Carbomer 940. Mix until batch is uniform. Stir for about 45 minutes before adding any other ingredients, and then neutralize the batch using alkalizer, e.g., triisopropanolamine. In the remaining water, that has been heated to 60° C., dissolve the PVP, (film former) conditioner, e.g., dimethicone copolyol and surfactant, e.g., PPG-10 methyl glucose ether. Stir this solution until it becomes clear, then add to the batch. Stir the batch for about 20 minutes until all lumps are gone.

The product may be used in either a leave-in or a rinse-out procedure. When used for a leave-in application, the product is applied to the hair, preferably in the form of a gel or a mousse, and dried on the hair.

When used in a rinse-out product, the formulation is applied to the hair for a period of time and rinsed from the hair. The hair may be shampooed to remove excess dye. The time and temperature of application may be varied depending of the effect desired. At room temperature and application times of 5–10 minutes, the coloring result is temporary and the color will be fully removed from the hair in one or two shampoos. A post-dyeing shampoo would not be used in this case.

For a more permanent effect, the product may be applied for up to 30–45 minutes under a hair dryer. The initial color result will be more intense under these conditions and the dye will survive several shampoos.

The following examples are given to further illustrate the present invention. It is to be understood, however, that this invention is not limited thereto.

The terminology used for the ingredients in the Examples marked with an asterisk is defined in the CTFA Cosmetic Ingredient Dictionary, Second Edition, Copyrighted 1973, 1977 published by The Cosmetic, Toiletry and Fragrance Association, Inc.

The following terms, appearing in the Examples having the meanings set forth below:

TMPD ®-Glycol = 2,2,4-trimethyl-1,3-pentanediol

NPG ®-Glycol = 2,2-dimethyl-1,3-propanediol

CHDM-R ®-Glycol = 1,4-cyclohexanedimethanol

EXAMPLE 1

Temporary/Semipermanent Hair Color Lotions

| Ingredient | % W/W | | | |
|---|---|---|---|---|
| | Ex. 1 | Ex. 2 | Ex. 3 | Ex. 4 |
| D.I. Water | 87.57 | 87.57 | 87.57 | 83.82 |
| Hydroxyethylcellulose | 1.100 | 1.100 | 1.100 | 1.100 |
| D & C Violet #2 | 0.035 | 0.035 | 0.035 | 0.035 |
| D & C Orange #4 | 0.300 | 0.300 | 0.300 | 0.300 |
| FD & C Yellow #6 | 0.045 | 0.045 | 0.045 | 0.045 |
| Citric Acid | 1.000 | 1.000 | 1.000 | 1.000 |
| Ammonium Lauryl Sulfate | 6.000 | 6.000 | 6.000 | 6.000 |
| Fragrance | 0.200 | 0.200 | 0.200 | 0.200 |
| TMPD ® - Glycol | 3.750 | — | — | 7.500 |
| NPG ® - Glycol | — | 3.750 | — | — |
| CHDM-R ® | — | — | 3.750 | — |
| | 100.000 | 100.000 | 100.000 | 100.000 |

The above compositions were prepared generally in accordance with the procedure previously recited in respect of lotions.

Temporary/Semipermanent Hair Color Styling Gel

| Ingredient | % W/W | | |
|---|---|---|---|
| | Ex. 5 | Ex. 6 | Ex. 7 |
| D.I. Water | 86.588 | 86.588 | 86.588 |
| EDTA | 0.005 | 0.005 | 0.005 |
| Benzophenone-3 | 0.005 | 0.005 | 0.005 |
| Phenoxyethanol | 0.200 | 0.200 | 0.200 |
| D & C Orange #4 | 0.120 | 0.120 | 0.120 |
| Ext. D & C Violet #2 | 0.014 | 0.014 | 0.014 |
| FD & C Yellow #6 | 0.018 | 0.018 | 0.018 |
| Laureth-23 | 1.000 | 1.000 | 1.000 |
| Fragrance | 0.150 | 0.150 | 0.150 |
| Carbomer 940 | 0.600 | 0.600 | 0.600 |
| Triisopropanolamine | 1.100 | 1.100 | 1.100 |
| Methylparaben | 0.200 | 0.200 | 0.200 |
| PVP | 2.500 | 2.500 | 2.500 |
| PPG-10 Methyl Glucose Ether | 1.000 | 1.000 | 1.000 |
| Dimethicone Copolyol | 1.500 | 1.500 | 1.500 |
| TMPD ® - Glycol | 5.000 | — | — |
| NPG ® - Glycol | — | 5.000 | — |
| CHDM-R ® | — | — | 5.000 |
| | 100.000 | 100.000 | 100.000 |

The above compositions were prepared generally in accordance with the procedure previously recited in respect of gels.

EXAMPLE 2

To determine whether the diols employed in the present invention as cosolvents at the concentration in the range of from about 2% to about 10% by weight based on the total weight of the colorant composition are a viable substitute for ethyl alcohol at a concentration of about 33.3% on the same weight basis the following compositions were prepared:

TABLE I

| Ingredient | W/W % | | | |
|---|---|---|---|---|
| | A | A-1 | A-2 | A-3 |
| D & C Yellow #10 | 0.084 | 0.084 | 0.084 | 0.084 |
| FD & C Yellow #6 | 0.112 | 0.112 | 0.112 | 0.112 |
| D & C Red #33 | 0.020 | 0.020 | 0.020 | 0.020 |
| Hydroxyethylcellulose | 1.100 | 1.100 | 1.100 | 1.100 |
| Citric Acid | 1.100 | 1.100 | 1.100 | 1.100 |
| Ammonium Lauryl Sulfate | 6.000 | 6.000 | 6.000 | 6.000 |
| Fragrance | 0.500 | 0.500 | 0.500 | 0.500 |
| Ethanol | 33.3 | — | — | — |
| TMPD ® -Glycol | — | 3.75 | — | — |
| NPG ® -Glycol | — | — | 3.75 | — |
| CHDM ® -R-Glycol | — | — | — | 3.75 |
| D.I. Water | QS 100 | QS 100 | QS 100 | QS 100 |

TABLE II

| Ingredient | W/W % | | | |
|---|---|---|---|---|
| | B | B-1 | B-2 | B-3 |
| Ext. D & C Violet #2 | 0.075 | 0.075 | 0.075 | 0.075 |
| D & C Green #5 | 0.100 | 0.100 | 0.100 | 0.100 |
| D & C Orange #4 | 0.090 | 0.090 | 0.090 | 0.090 |
| D & C Yellow #10 | 0.050 | 0.050 | 0.050 | 0.050 |
| D & C Red #4 | 0.015 | 0.015 | 0.015 | 0.015 |
| Hydroxyethylcellulose | 1.100 | 1.100 | 1.100 | 1.100 |
| Citric Acid | 1.100 | 1.100 | 1.100 | 1.100 |
| Ammonium Lauryl Sulfate | 6.000 | 6.000 | 6.000 | 6.000 |
| Fragrance | 0.500 | 0.500 | 0.500 | 0.500 |
| Ethanol | 33.3 | — | — | — |
| TMPD ® -Glycol | — | 3.75 | — | — |
| NPG ® -Glycol | — | — | 3.75 | — |
| CHDM ® -R-Glycol | — | — | — | 3.75 |
| D.I. Water | QS 100 | QS 100 | QS 100 | QS 100 |

Using each of the above compositions A to A-3 and B to B-3, gray and pigmented hair was colored using the following procedure:

I. Swatches were cut to 3-4 grams in weight.

II. Hair was placed in a dish with about 10-15 grams of coloring solution, with working of the solution through the hair swatches using finger tips to make sure each strand of hair was well saturated. The solution was applied for about 30 minutes at 50° C., to obtain a semi-permanent color.

III. The hair swatches were thereafter rinsed thoroughly using warm water.

The results of these dyeing tests are summarized in Table III below. The L, A and B values are the standard Hunter Tristimulus Values, L indicating the degree of lightness, A the degree of red or green and B the degree of yellow or blue. If A is positive the color is red, while if A is negative the color is green. If B is positive the color is yellow, while a negative value for B indicates the color is blue.

TABLE III

| SAMPLE | ORIGINAL (UNTREATED HAIR) | | | AFTER TREATMENT* | | |
|---|---|---|---|---|---|---|
| | L | A | B | L | A | B |
| Gray Hair | | | | | | |
| Composition A | 32.47 | −.74 | 6.52 | 31.10 | 1.63 | 9.50 |
| Composition A-1 | 33.69 | −.71 | 6.47 | 29.81 | 2.76 | 9.64 |
| Composition A-2 | 31.53 | −.31 | 6.09 | 28.95 | −.99 | 8.68 |
| Composition A-3 | 32.15 | −1.11 | 6.08 | 29.98 | 2.63 | 10.16 |
| Pigmented Hair | | | | | | |
| Composition A | 12.30 | 1.64 | 2.81 | 12.38 | 2.64 | 3.30 |
| Composition A-1 | 12.56 | −.88 | 2.56 | 12.12 | 2.87 | 3.03 |
| Composition A-2 | 12.33 | 1.30 | 2.68 | 12.55 | 2.67 | 3.47 |
| Composition A-3 | 12.28 | −.97 | 2.73 | 11.63 | 2.51 | 2.98 |
| Gray Hair | | | | | | |
| Composition B | 36.24 | −.63 | 5.59 | 25.69 | 1.43 | 4.92 |
| Composition B-1 | 36.53 | −.65 | 5.59 | 24.55 | 1.95 | 4.14 |
| Composition B-2 | 35.98 | −.66 | 5.68 | 28.55 | 1.30 | 5.40 |
| Composition B-3 | 35.88 | −.70 | 5.50 | 29.68 | 1.30 | 5.55 |

TABLE III-continued

| SAMPLE | ORIGINAL (UNTREATED HAIR) | | | AFTER TREATMENT* | | |
|---|---|---|---|---|---|---|
| | L | A | B | L | A | B |
| Pigmented Hair | | | | | | |
| Composition B | 15.15 | 1.42 | 1.50 | 14.98 | 1.38 | 1.34 |
| Composition B-1 | 14.80 | 1.33 | 1.18 | 13.81 | 1.38 | −.75 |
| Composition B-2 | 14.92 | −1.52 | 1.18 | 14.75 | −.99 | −.99 |
| Composition B-3 | 15.27 | 1.49 | 1.33 | 14.98 | 1.05 | 1.01 |

*30 minutes at 50° C.

As will be apparent from the above results the diols of the present invention at a concentration in the range of from about 2% to about 10% (and particularly at a concentration of 3.75%) when employed as a cosolvent give dye deposits on hair that are comparable to that obtained when ethanol, at a concentration of 33.3%, is used as the cosolvent. Moreover, with the diol TMPD ®-Glycol, i.e., 2,2,4-trimethyl-1,3-pentanediol, there was a significant improvement in the color deposit on bleached, gray and pigmented hair. To obtain a temporary color, the solutions would be applied for about 15 minutes at room temperature.

EXAMPLE 3

A similar study was done using coloring composition containing the individual dyes D&C Red #33, D&C Orange #4 and D&C Yellow #10, respectively. In this instance, the diol employed was TMP ®-Glycol at a concentration of 3.75% by weight based on the total weight of the coloring composition as compared with compositions containing 33.3% ethanol. The composition tested are given in Table IV below.

TABLE IV

| Ingredient | Concentration, W/W % | | | | | |
|---|---|---|---|---|---|---|
| | D & C Red #33 (A) | D & C Red #33 (B) | D & C Orange #4 (A) | D & C Orange #4 (B) | D & C Yellow #10 (A) | D & C Yellow #10 (B) |
| D & C Red #33 | 0.100 | 0.100 | | | | |
| Citric acid | 1.000 | 1.000 | | | | |
| Hydroxyethyl-cellulose | 1.100 | 1.100 | | | | |
| Ammonium Lauryl Sulfate | 6.000 | 6.000 | | | | |
| TMPD ® - Glycol | 3.75 | | | | | |
| Ethanol | | 33.000 | | | | |
| Fragrance | 0.200 | 0.200 | | | | |
| D.I. Water | QS 100 | QS 100 | | | | |
| D & C Orange #4 | | | 0.100 | 0.100 | | |
| Citric Acid | | | 1.000 | 1.000 | | |
| Hydroxyethyl-cellulose | | | 1.100 | 1.100 | | |
| Ammonium Lauryl Sulfate | | | 6.000 | 6.000 | | |
| TMPD ® - Glycol | | | 3.750 | | | |
| Ethanol | | | | 33.000 | | |
| Fragrance | | | 0.200 | 0.200 | | |
| D.I. Water | | | QS 100 | QS 100 | | |
| D & C Yellow #10 | | | | | 0.100 | 0.100 |
| Citric cid | | | | | 1.000 | 1.000 |
| Hydroxyethyl-cellulose | | | | | 1.100 | 1.100 |
| Ammonium Lauryl Sulfate | | | | | 6.000 | 6.000 |
| TMPD ® - Glycol | | | | | 3.750 | |
| Ethanol | | | | | | 33.300 |
| Fragrance | | | | | 0.200 | 0.200 |
| D.I. Water | | | | | QS 100 | QS 100 |

Using each of the composition given in Table IV gray hair, pigmented hair and bleached hair were colored using the procedure of Example 2.

The results of these dyeing tests are summarized in Table V below. As previously discussed the L, A and B values recorded in Table V are Hunter Tristimulus values.

TABLE V

| SAMPLE | ORIGINAL (UNTREATED HAIR) | | | AFTER TREATMENT* | | |
|---|---|---|---|---|---|---|
| | L | A | B | L | A | B |
| Gray Hair | | | | | | |
| D & C Red #33 (A) | 33.74 | −.11 | 6.22 | 24.90 | 7.15 | 12.20 |
| D & C Red #33 (B) | 32.10 | −.50 | 6.00 | 27.56 | 6.53 | 11.67 |
| Pigmented Hair | | | | | | |
| D & C Orange #4 (A) | 34.04 | −.46 | 6.44 | 26.29 | 10.14 | 1.21 |
| D & C Orange #4 (B) | 32.67 | −.30 | 5.91 | 28.32 | 7.29 | 2.16 |
| Bleached Hair | | | | | | |
| D & C Yellow #10 (B) | 62.01 | −2.21 | 18.59 | 60.70 | −10.46 | 30.74 |
| D & C Yellow #10 (B) | 61.92 | −2.33 | 15.23 | 61.86 | −12.42 | 31.68 |
| Gray Hair | | | | | | |
| D & C Yellow #10 (A) | 31.52 | −.69 | 5.84 | 33.23 | −4.65 | 13.46 |
| D & C Yellow #10 (B) | 29.93 | .74 | 5.41 | 30.86 | −4.25 | 11.74 |

*30 minutes at 50° C.

As is evident from Table V this study confirms the fact that TMPD ®-Glycol in place of ethanol enhances the color that is delivered to the hair.

What is claimed is:

1. A temporary or semipermanent hair coloring composition comprising an aqueous vehicle having incorporated therein a hair coloring component comprising one or more hair colorants selected from the group consisting of water-soluble temporary and water-soluble semipermanent hair colorants and mixtures thereof, in amount sufficient to color hair, said composition also containing as a cosolvent for said hair colorants from about 2 to about 15% by weight of a diol, said diol being selected from the group consisting of branched chain aliphatic hydrocarbon diols and having from 5 to 8 carbon atoms and bis(hydroxyalkyl) cycloalkanes having from 7 to 14 carbon atoms, said diol being present in said composition in a concentration to effectively function as a cosolvent for said hair colorants.

2. A composition according to claim 1, wherein said bis(hydroxyalkyl) cycloalkane has from 8 to 12 carbon atoms.

3. A composition according to claim 2 wherein the cycloalkane moiety of said bis(hydroxyalkyl) cycloalkane has 6 carbon atoms.

4. A composition according to claim 3 wherein the alkyl moiety of the hydroxyalkyl group of said bis(hydroxyalkyl) cycloalkane is a lower alkyl group containing 1 to 4 carbon atoms.

5. A composition according to claim 1 wherein said aqueous vehicle is a non-ethanolic vehicle.

6. A composition according to claim 1 wherein said diol is present in said composition at a concentration in the range of from about 2% to about 10% by weight.

7. A composition according to claim 1 wherein said hair colorants are direct dyes.

8. A composition according to claim 1 wherein said diol is selected from the group consisting of 2,2,4-trimethyl-1, 3-pentanediol; 2,2-dimethyl-1,3-propanediol; 1,4-cyclohexanedimethanol, and 2-ethyl-1,3-hexanediol.

9. A composition according to claim 1 in the form of a gel.

10. A composition according to claim 1 in the form of a lotion.

11. A process for coloring hair comprising applying to said hair the composition of claim 1 in an amount effective to provide a temporary or semipermanent color to said hair.

12. The composition of claim 1 wherein the hair colorant is present in an amount of from 0.01 to about 4% by weight of the composition.

13. The composition of claim 1 wherein the hair colorants are selected from the group consisting of D&C Orange #4; FD&C Yellow #6; External D&C Violet #2; FD&C Red #4; FD&C Yellow #5; D&C Red #33; FD&C Blue #1; D&C Yellow 10, and D&C Green #5.

* * * * *